United States Patent
Xu et al.

(10) Patent No.: US 9,243,883 B2
(45) Date of Patent: Jan. 26, 2016

(54) APPARATUS AND METHOD FOR CONDUCTING AND REAL-TIME APPLICATION OF EC PROBE CALIBRATION

(71) Applicant: Olympus NDT, Inc., Waltham, MA (US)

(72) Inventors: Xiangdeng Xu, Acton, MA (US); Paul DeAngelo, West Bridgewater, MA (US)

(73) Assignee: OLYMPUS NDT, INC., Waltham, MA (US)

( * ) Notice: Subject to any disclaimer, the term of this patent is extended or adjusted under 35 U.S.C. 154(b) by 117 days.

(21) Appl. No.: 14/227,005

(22) Filed: Mar. 27, 2014

(65) Prior Publication Data

US 2015/0276371 A1    Oct. 1, 2015

(51) Int. Cl.
*G01R 35/00* (2006.01)
*G01B 7/06* (2006.01)
*G01N 27/90* (2006.01)

(52) U.S. Cl.
CPC . *G01B 7/10* (2013.01); *G01N 27/90* (2013.01)

(58) Field of Classification Search
CPC ......... G01B 7/10; G01N 27/90; G01N 33/20; G01N 2201/127; G01R 35/00; G01R 35/005; G01R 33/028; G01R 33/1223; G01R 33/0283; G01R 33/0286
See application file for complete search history.

(56) References Cited

U.S. PATENT DOCUMENTS

| | | | | |
|---|---|---|---|---|
| 4,425,545 A | * | 1/1984 | Scalese | G01R 35/007 324/202 |
| 2010/0312494 A1 | * | 12/2010 | Korukonda | G01N 27/9046 702/38 |
| 2014/0117982 A1 | * | 5/2014 | Budiarto | G01B 7/105 324/229 |

OTHER PUBLICATIONS

*Standard Test Method for Determining Electrical Conductivity Using the Electromagnetic (Eddy-Current) Method*, Copyright by ASTM International, Thu Mar. 20 16:43:29 EDT 2014 1 Designation: E1004-09.

* cited by examiner

*Primary Examiner* — Son Le
(74) *Attorney, Agent, or Firm* — Ostrolenk Faber LLP (57) ABSTRACT

A system and method for carrying out non-destructive testing and inspection of test objects to inspect for anomaly using eddy current instruments, the instrument has an on-board calibration module configured to provide probe-specific conductivity or thickness correction data over a plurality of testing points of a standard block having known conductivity and thicknesses using the same physical probe as is used for the inspection measurements. When the same probe induces eddy current into a test object, the instrument having a processor or computing unit, computes a conductivity or thickness value, corrected by the above said correction data pertaining to the specific probe.

19 Claims, 5 Drawing Sheets

APPARATUS AND METHOD FOR CONDUCTING AND REAL-TIME APPLICATION OF EC PROBE CALIBRATION

FIELD OF THE INVENTION

The present invention relates to non-destructive testing and inspection instruments (NDT/NDI) and more particularly to a method to generate probe-instrument specific calibration values and to apply the same to the instrument.

BACKGROUND OF THE INVENTION

The measurement data from NDT/NDI devices used for the routine monitoring of structural integrity must be of sufficient accuracy to allow a valid assessment to be made of the conditions of the structure under test. Examples of such structures are pipes and vessels widely used in the petrochemical and other industries. Examples of measurement data are pipe wall thickness and other geometric conditions, including, but not limited to, the presence of irregular surfaces (e.g. corrosion, oxide, etc.) and flaws (e.g. porosity, cracks, etc.).

Often, the decision to perform or not perform maintenance on a structure is made based on the assessment of the measurement data. Therefore, the measurement accuracy will have a direct impact on the decision. The consequence of inaccurate measurement data that underestimates an unfavorable condition of a structure can result in failures occurring before maintenance is performed. Conversely, inaccurate measurement data that overestimates an unfavorable condition of a structure can result in performing expensive and unnecessary maintenance.

One of the most common NDT/NDI devices used for assessing structural integrity is an eddy current (herein after as "EC") instrument for examining conductivity of conductive materials. In a typical eddy current inspection operation, an eddy current array probe, comprising a plurality of coils, is placed adjacent to the surface of a material under inspection. At the start of an inspection operation, an NDI instrument coupled to the eddy current probe energizes one or more coils. This, in turn, induces a current in the material under inspection. One or more coils within the probe array then sense this induced current and provide a measurement signal to the NDI instrument. By measuring the current induced in a material under inspection, the impedance or conductivity of said material can be calculated. Further, by tracking the impedance of a material under inspection as the probe is moved along the surface of said material flaws and defects within said material can be found and analyzed for anomaly reading of the impedance or conductivity.

The specific challenge herein dealt with is that the instrument needs to be calibrated for all different types of EC probes designed to work with instrument.

One conventional solution for EC probe calibration employs pre-defined static data tables to compensate for the time distortion; however, this solution has the drawback of not accounting for actual conditions of the probe in use since it only calibrates for one type of the probe. However, all probes of the same type can differ due to various reasons including probe wear and manufacturing variances in probe population. The conventional method also does not account for any drifts caused by change in environment, such as temperature.

The conventional method of determining conductivity and thickness is of standard in the field of conductivity measurements using eddy current. One can refer to *ASTM E1004—09 Standard Test Method for Determining Electrical Conductivity Using the Electromagnetic (Eddy-Current) Method*, Active Standard ASTM E1004 | Developed by Subcommittee: E07.07, Book of Standards Volume: 03.03.

Current empirical calibration data table using a pre-determined data table, use empirical methods of deriving data to generate the Table. The predetermined Table is generated by using conductivity measurement methods on a batch of typical eddy current probes of one model. It is then used for hundreds of the probes of the same model for many years. The existing calibration table is herein referred to as the "Empirical Table". Once can refer to one of these existing standard, or particularly, *AC Conductivity Standards for the Calibration of Eddy-Current Conductivity Meters*", by A E Drake and A C Lynch, 1987 *J. Phys. E: Sci. Instrum.* 20 137. doi:10.1088/0022-3735/20/2/003.

Accordingly, a solution that overcomes the drawbacks described above and results in advantages highly valued by potentially affected industrial and public infrastructure concerns, needs to:

a. improve measurement accuracy by using probe-specific reference tables;

b. allow support and usage of third party, out-of-design-spec probes; and c. allow customer additions of future new probes.

SUMMARY OF THE INVENTION

Accordingly, it is an object of the present invention to provide an instrument and method for obtaining more accurate probe specific calibration data for eddy current conductivity and thickness testing.

It is a further object of the invention to provide an instrument and method that allows EC instrument to be compatible more probes that are not calibrated by the manufacturers.

Yet another object of the invention is to provide instrument and method to improve measurement accuracy of generic probe which a pre-defined calibration data is unknown.

The foregoing and other objects of the invention are realized with a conductivity and thickness measuring system for measuring the conductivity and thicknesses of calibration blocks (test objects). The system includes a calibration module which is configured to provide conductivity correction data over a plurality of block's testing points, obtained from one or more objects having known conductivity and thicknesses. A probe configured to launch eddy currents over a test object (a standard block) and to receive returning signal is employed, to produce an electrical output representative of the returning waves. An instrument, including control and computation hardware and software, is coupled to the probe and is configured to compute values of conductivity and thickness of the standard block at a plurality of standard testing points. A correction module associated with the instrument and configured to receive the computed data from the calibration module is used to correct the conductivity computed by the instrument, based on the conductivity correction data provided by the calibration module.

Further, the dynamic correction data can be provided in the form of a plurality of discreet correction values and those values can be used to compute correction values, needed to correct the conductivity as the measurement is being made. Alternatively, linear equations or higher order polynomials can be fitted to dynamic correction data for each probe and these equations can be used to compute the needed conductivity correction information in real-time as the measurement is being made.

Other features and advantages of the present invention will become apparent from the following description of the invention that refers to the accompanying drawings.

DETAILED DESCRIPTION OF THE INVENTION

In order to assist the understanding of presently disclosed EC probe calibration method, the following description is given in reference to FIGS. 1-5.

It should be noted that 'sensor', 'probe' and 'coil' are herein used in the present disclosure interchangeably. The term 'real-time measurement' is used in the present disclosure to mean the immediate measurement result provided to the user or external device by measurement device 100 (FIG. 1) using one or more probe driving/sensing cycles. The measurement result may be provided to the user by means of display 12, an integral audio device (not shown), and/or an external device by means of input/output port. The measurement result may be comprised of, but not limited to, values representing conductivity, thickness and/or an alarm indication.

Figure 1:
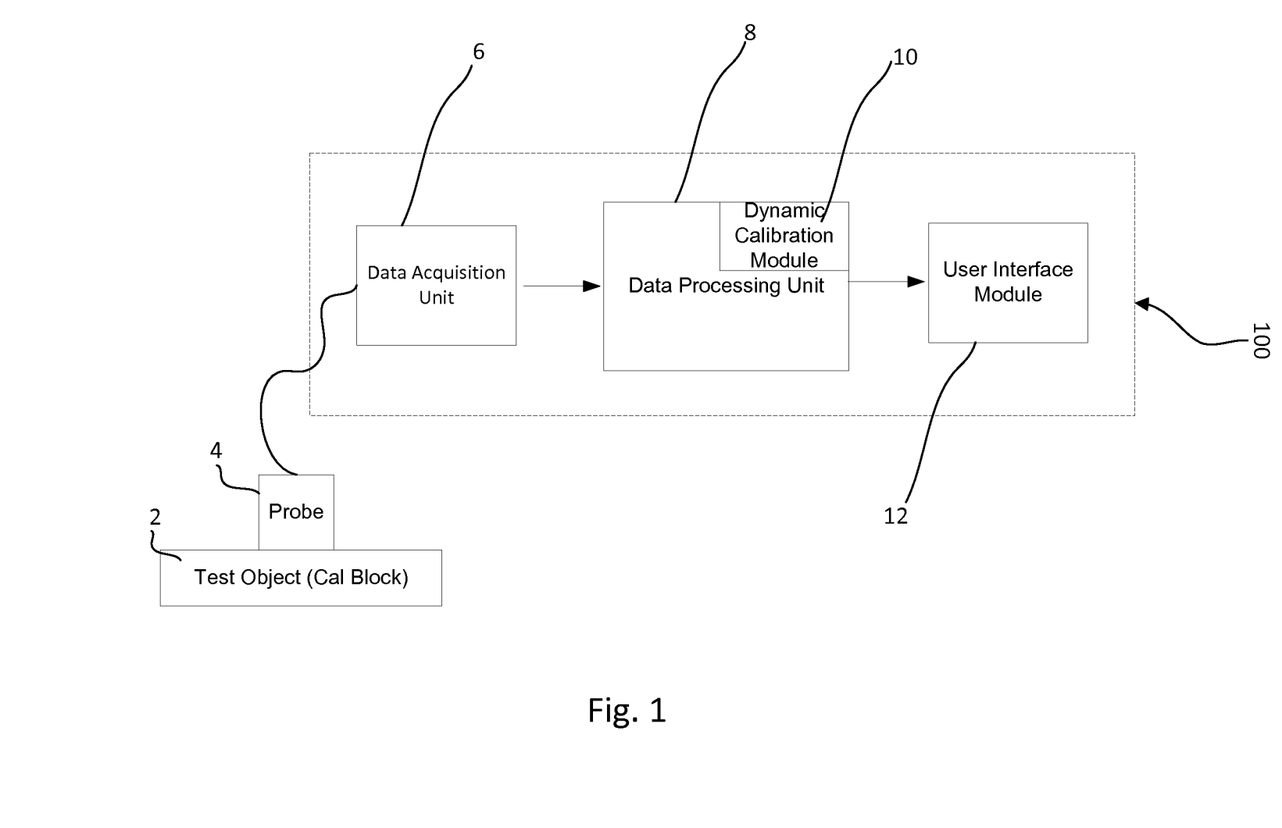
FIG. 1 is a diagram of an Eddy Current instrument including the dynamic calibration module according to the present disclosure.

Referring to FIG. 1, the presently disclosed EC probe calibration method as disclosed is used in conjunction with an Eddy Current transducer inspection device 100. The inspection system comprises an eddy current probe 4; a Data Acquisition Unit 6; a Data Processing Unit 8, which includes a Dynamic Calibration Module 10, wherein the algorithm of the present disclosure is executed; a Display Module 12. A target test object 2 can be one of the standard calibration block or a real test target.

One of the novel aspects of the present disclosure is a system and method employing a software program executing a process that may be used for producing and employing calibrated probe-specific phase/magnitude vs. conductivity mapping data tables, henceforth referred to as Base Reference Tables (later as off-line Tables) for probes. The Tables, in existing practice, is employed by eddy current conductivity & thickness measuring apparatus as off-line look-up tables. However, the concept of the off-line Tables is different from the dynamic Tables herein disclosed. This is because the dynamic Tables are not limited to the kinds of off-line Tables made available with the instruments, and can be generated by operator and stored in the present instruments based on unlimited number of calibration blocks.

Another important difference that's worth noting is that the off-line Tables are used in the conductivity and thickness measurement calculation, generic to all probes of one certain type. Due to the variation of probe hardware circuitry, for the same test target, the detected EC signal (phase angle, magnitude) could be slightly different for each individual probe. Hence, the dynamically generated Tables in the present disclosure can support applications of probe-specific Base Reference Tables, which may be essential for accurate conductivity and thickness measurement.

Referring again to FIG. 1, for each calibration block associated with a type of measurement, one can choose to have the instrument generate a probe-block specific reference table; or choose to use an existing table. During a calibration procedure on a standard block, EC probe 4 picks up the induced electrical signal and transmits it to the Data Acquisition Unit 6. Data Acquisition Unit 6 extracts the desired info (phase angle, magnitude) and passes it to the Data Processing Unit 8. Dynamic Calibration Module 10 can be devised directly with the original design of instrument 100, or it can be devised as a software module separately loaded on the data processing unit 8 of an existing instrument 100. Data Processing Unit 8, collects the user input data of target conductivity values and the actual acquired EC signal info, processes the data, creates the dynamic Base Reference Tables and stores the tables inside the measurement device, likely in a memory (not shown).

During the measurement sessions, the instrument employs the newly created base reference tables for the probe-block to conduct measurement calculation of conductivity and thickness. The final measurement results is sent to the Display Module 12 and presented to the operator.

Figure 2:
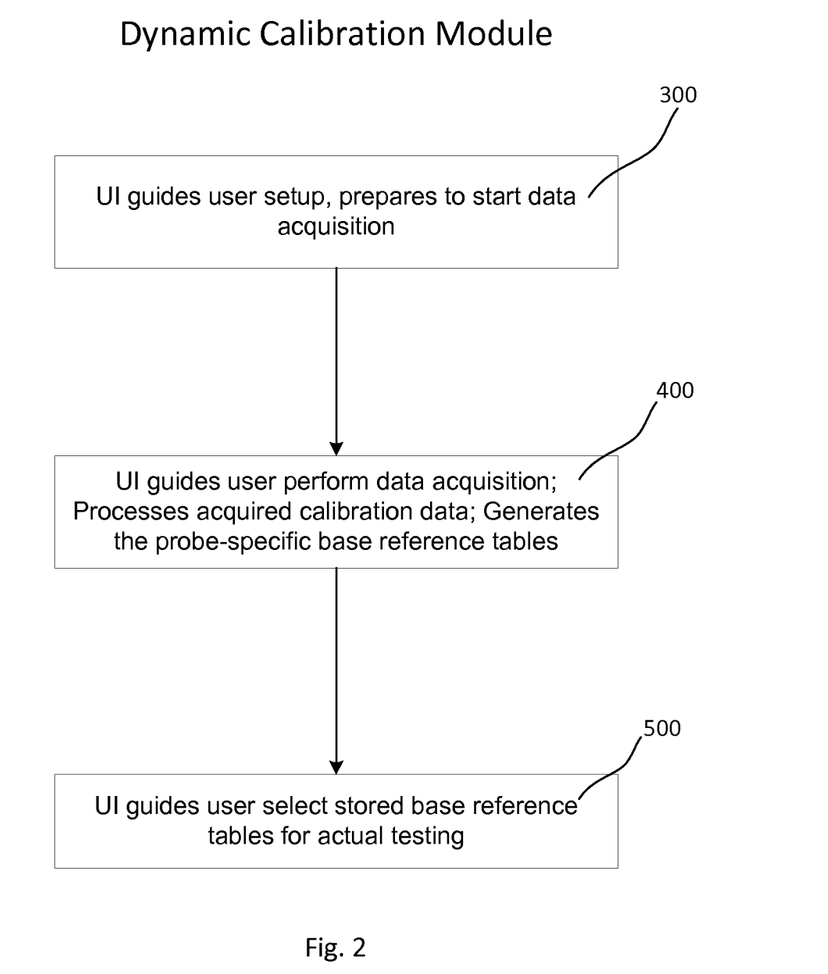
FIG. 2 is a diagram showing the functional modules used for deriving and employing EC probe calibrated base reference table according to the present invention.

Reference is now made to FIG. 2, which illustrates the process in a flowchart including the steps executed by Dynamic Calibration Module 10. It contains three sub-components, i.e. a Data Acquisition Preparation block 300, Data Acquisition and Table Creation block 400 and a Base Reference Table Utilization block 500. The details about blocks 300, 400, 500 are further explained in FIG. 3, FIG. 4, and FIG. 5, respectively.

Figure 3:
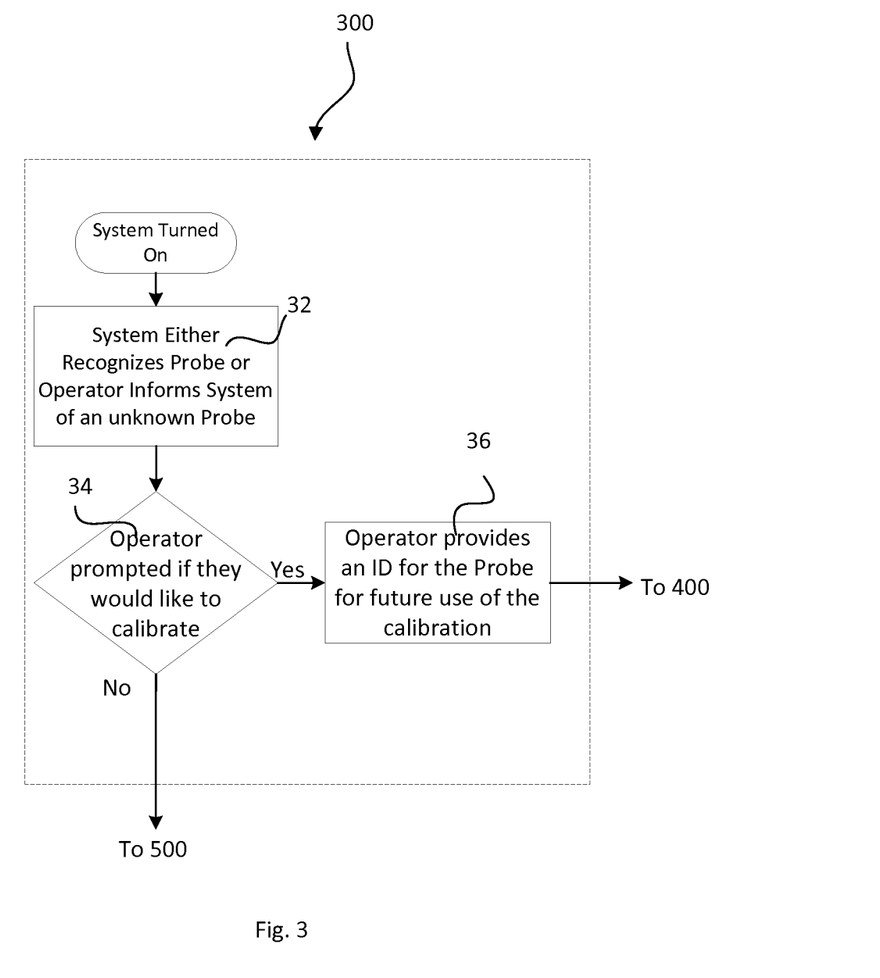
FIG. 3 is a flow chart showing the steps required for setting up the dynamic calibration module, preparing input calibration data from the operator.

FIG. 3 shows the details how one can use the user interface 12, following a user setup procedure and to prepare to start data acquisition via block 300. After the instrument is turned on, in step 32 the instrument obtains the information pertaining to the probe 4 either directly from the probe or through the operator's input via user interface 12. Then the operator is prompted whether he/she wants to do calibration or not in step 34. As mentioned above, one can choose to use a default table, or existing calibration table or choose to create a new probe-block specific calibration table. If doing a new calibration, or creating a new table is not desired, the procedure goes to block 500 in FIG. 5; otherwise, in step 36, operator is prompted to provide an ID for the probe for future use of the calibration, then branches to process 400 for calibration.

It can be understood that the conductivity or thickness correction data for each testing point of the block can be obtained by repeated measurements and by the averaging of repeated measurements at the same testing point.

Figure 4:
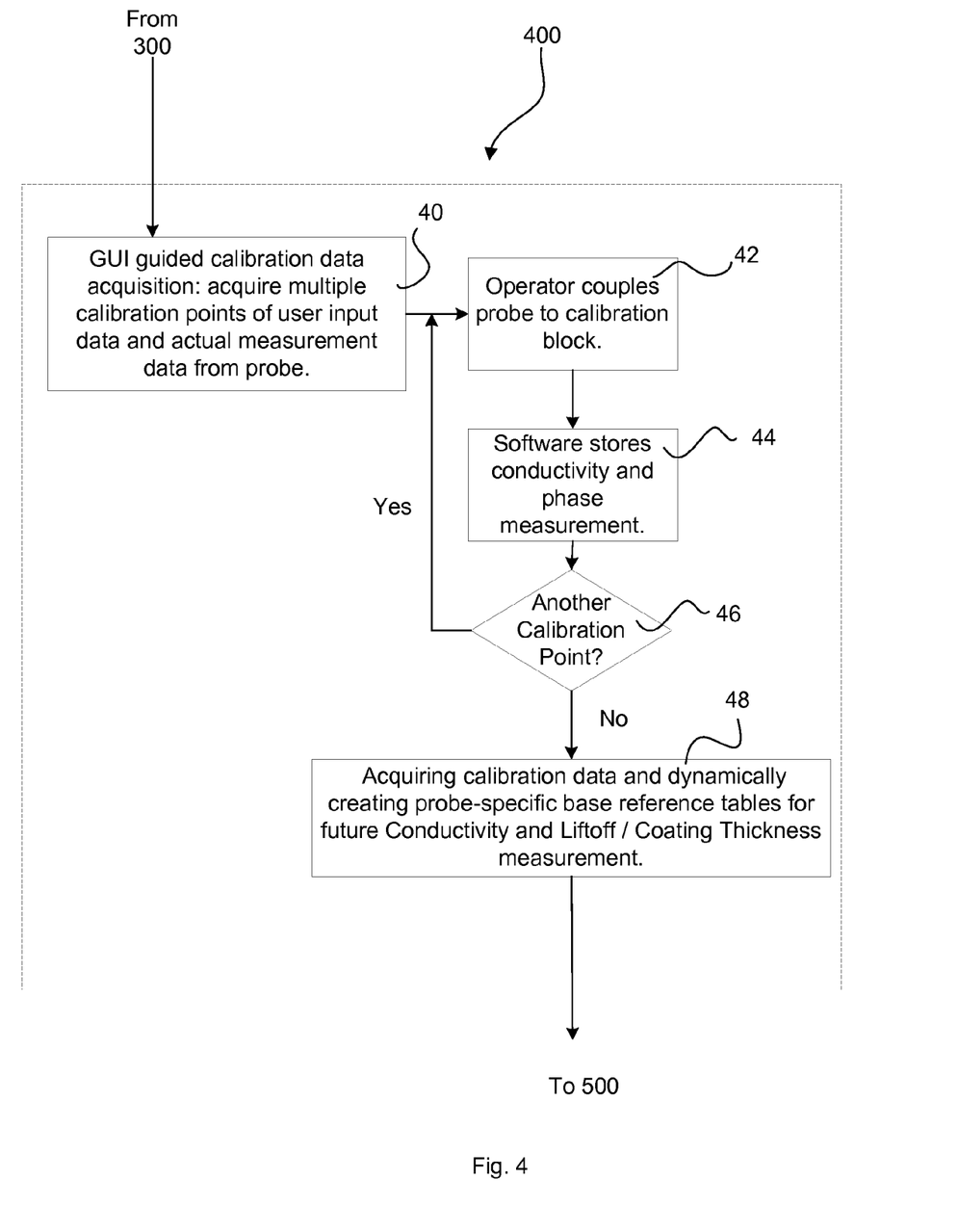
FIG. 4 is a flow chart showing steps required for acquiring input calibration data from the operator, deriving and creating the Probe-Specific base reference tables

Reference is now turned to FIG. 4. FIG. 4 shows the detailed process executed by dynamic calibration module 10 to instruct user interface to guide user perform data acquisition, and to process acquired calibration data, and generate the probe-specific base reference tables (process 400 in FIG. 2). When data acquisition process starts, in step 40, calibration module 10 instructs UI 12 to guide the operator to acquire calibration data steps by step. The data acquisition unit 6 collects user input data and actual measurement data from probe 4 for the following calibration points. In step 42, the operator couples the probe to a calibration block; then in step 44, the system stores the user input value of the calibration block's conductivity and measured phase angle and magnitude. In step 46 it checks whether another calibration point needs to be acquired. If yes, the process goes back to repeat step 42; otherwise, in step 48, module 10 processes all acquired calibration data points, creates the base reference tables including phase angle vs. conductivity table, magnitude vs. conductivity table, and relative magnitude vs. thickness table (48). After this process is completed, module 10 switches to block for process 500.

Figure 5:
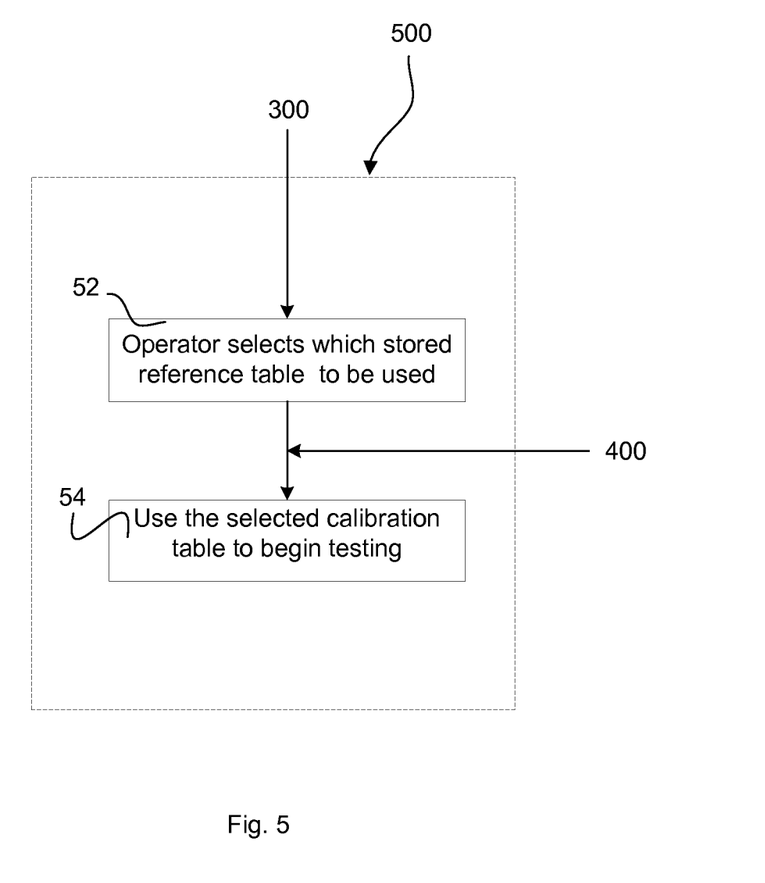
FIG. 5 is a flow chart showing the module and steps required for the application of the Probe-Specific base reference tables during the measurement calculation phase.

Referring to FIG. 5, detail of the process included in block 500 executed by dynamic calibration module 10 is shown. According to FIG. 5, in step 52, calibration module 10 instructs UI 12 to prompt the operator to choose either the pre-defined base reference tables or the presently calibrated probe-specific base reference tables should be used for an actual testing. Once the choice is decided, the instrument loads the selected tables into active table buffer and starts to use them for actual testing measurement calculations in step 54.

Other arrangements of embodiments of the invention include software programs to perform the method embodiment steps and operations summarized above and disclosed in detail below. More particularly, a computer program is one embodiment that has a computer-readable medium including computer program logic encoded thereon that when encoded and executed in a computerized device provides associated operations providing EC probe calibration as explained herein. The computer program logic, when executed on at least one processor with a computing system, causes the processor to perform the operations (e.g., the methods and algorithms) indicated herein as embodiments of the invention. Such arrangements of the invention are typically provided as software, code and/or other data structures arranged or encoded on a computer readable medium such as but not limited to an optical medium (e.g., CD-ROM, DVD-ROM, etc.), floppy or hard disk, a so-called "flash" (i.e., solid state) memory medium, or other physical medium, such as but not limited to firmware or microcode in one or more of ROM or RAM or PROM chips, or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities may also provide the system of the invention. The system of the invention may be distributed between many software processes on several data communications devices, or all processes may run on a small set of dedicated computers or on one computer alone.

It should also be understood that embodiments involving different methods of deriving correction data should be within the scope of the present disclosure. For example, the conductivity or thickness correction data is provided in the form of a plurality of discrete correction values, and wherein the data processing or computing unit is configured to correct the measured conductivity value by locating a corresponding discrete conductivity or thickness correlation data and/or by computing a correction conductivity or thickness data by interpolation using adjacent ones of the correction data. Another example can be that the corrected values of conductivity or thickness are derived from linear relationships which are fitted to the correction data.

It is to be understood that embodiments of the invention may be embodied strictly as a software program, as software and hardware, or as hardware and/or circuitry alone. The features disclosed and explained herein may be employed in computerized devices and software systems for such devices.

The embodiments of the eddy current system can be used to perform non-destructive testing to inspect the integrity of the test objects based on anomaly in the values of conductivity and/or thickness.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. An eddy current system for measuring conductivity or thicknesses of test objects of different categories, comprising:
   a plurality of standard test blocks matching categories of the test objects, the blocks all having corresponding standard testing points, each with target values of conductivity and thickness;
   a probe configured to excite eddy current into one of the blocks, one of testing points at a time, to sense response signals and to produce an electrical output representative of the response signals;
   a data acquisition unit producing amplitude and phase values based on the response signals;
   a computation unit configured to produce values of un-calibrated values of conductivity or thickness for the corresponding testing point of the corresponding block,
   a calibration module configured to provide conductivity or thickness correction data specific to the probe, based on the target values and the un-calibrated values of conductivity or thickness;
   wherein the computation unit is further configured to be calibrated according to the correction data, and is configure to conduct tests by using the probe on the test objects of corresponding category of the one of the blocks.

2. The eddy current system of claim 1, in which the probe is an eddy current probe.

3. The eddy current system of claim 1, in which the conductivity or thickness correction data is provided in the form of a plurality of discrete correction values, and wherein the computation unit is configured to correct the measured conductivity value by locating a corresponding discrete conductivity or thickness correlation data and/or by computing a correction conductivity or thickness data by interpolation using adjacent ones of the correction data.

4. The eddy current system of claim 1, in which the conductivity or thickness correction data for each testing point of the block and are obtained by repeated measurements and by the averaging of repeated measurements at the same testing point.

5. The eddy current system of claim 1, wherein the corrected values of conductivity or thickness are derived from linear equations which are fitted to the correction data.

6. The eddy current system of claim 1, wherein the calibration module comprises a data table.

7. The eddy current system of claim 1, wherein the system is configured to perform non-destructive testing to inspect the integrity of the test objects based on anomaly in conductivity or thickness.

8. The eddy current system of claim 1, including probe identification data of the probe and a memory storing multiple stored correction data for a plurality of probes, each stored correction data being identified by a corresponding probe identification data.

9. The eddy current system of claim 1, including a memory integrated with said probe which stores the correction data therein.

10. The eddy current system of claim 1, including a user interface which prompts an option whether to calibrate on the probe or not, and the choosing of calibrating the probe initiates the calibration module.

11. A method of measuring conductivity or thicknesses of a plurality of test objects by using an eddy current instrument, comprising the steps of:
inducing eddy-current into a test object with a probe and receiving returning signals and producing an electrical output representative of the returning signals;
providing conductivity or thickness correction data, specific to the probe, based on the measurement over a plurality of testing points on a standard block, the block is in the same category as of the test objects and having known conductivity or thicknesses;
conducting plurality of eddy current tests over the plurality of the test objects, using the same probe, computing a conductivity or thickness value based on the received signals for each of the test object; and,
using the correction data obtained relative to the objects and correcting the conductivity or thickness that has been computed.

12. The method for claim 11, further including providing the conductivity or thickness correction data in the form of a plurality of discreet correction values and using interpolation to correct the conductivity computed for the test object.

13. The method of claim 11, including obtaining the correction data for each testing point of the block by repeated measurements and by averaging the repeated measurements at the same testing points.

14. The method of claim 11, including providing a user interface by which it is prompted to an operator whether to calibrate on the probe.

15. The method of claim 11, including calculating the corrected value from linear equations which have been pre-fitted to correction data.

16. The method of claim 11, including performing non-destructive testing of the test object to inspect anomaly thereof by measuring the conductivity or thickness of the test object at various locations thereon.

17. The method of claim 11, further including obtaining the correction data by reading existing probe identification data associated with said probe being used, and selecting said correction data associated with said probe from a memory containing the correction data for a plurality of probes.

18. The method of claim 11, including storing said correction data in a memory module integrated with said probe.

19. The method of claim 11, including storing said correction data in a memory module integrated with the instrument, corresponding to an identification of the probe.

* * * * *

UNITED STATES PATENT AND TRADEMARK OFFICE
CERTIFICATE OF CORRECTION

| | | |
|---|---|---|
| PATENT NO. | : 9,243,883 B2 | Page 1 of 1 |
| APPLICATION NO. | : 14/227005 | |
| DATED | : January 26, 2016 | |
| INVENTOR(S) | : Xiangdong Xu and Paul DeAngelo | |

It is certified that error appears in the above-identified patent and that said Letters Patent is hereby corrected as shown below:

Title page, item (72), please correct inventor name as follows:

"Xiangdeng Xu" should be replaced by "Xiangdong Xu".

Signed and Sealed this
Twenty-sixth Day of April, 2016

Michelle K. Lee
*Director of the United States Patent and Trademark Office*